(12) United States Patent
Holzner et al.

(10) Patent No.: US 8,994,717 B2
(45) Date of Patent: Mar. 31, 2015

(54) METHOD FOR MODELING AN INDIVIDUAL DENTAL PROSTHESIS

(75) Inventors: Stephan Holzner, Hohenschäftlarn (DE); Gerhard Weber, Pürgen (DE)

(73) Assignee: Straumann Holding AG, Basel (CH)

( * ) Notice: Subject to any disclaimer, the term of this patent is extended or adjusted under 35 U.S.C. 154(b) by 1225 days.

(21) Appl. No.: 12/864,362

(22) PCT Filed: Jan. 26, 2009

(86) PCT No.: PCT/EP2009/000478
§ 371 (c)(1),
(2), (4) Date: Oct. 13, 2010

(87) PCT Pub. No.: WO2009/092613
PCT Pub. Date: Jul. 30, 2009

(65) Prior Publication Data
US 2011/0136080 A1 Jun. 9, 2011

(30) Foreign Application Priority Data
Jan. 25, 2008 (DE) .......................... 10 2008 006 048

(51) Int. Cl.
*G06T 15/00* (2011.01)
*A61C 13/00* (2006.01)
(Continued)

(52) U.S. Cl.
CPC ........... *A61C 13/0004* (2013.01); *A61C 8/0048* (2013.01); *A61C 8/005* (2013.01); *A61C 9/0046* (2013.01)
USPC .......................................................... 345/419

(58) Field of Classification Search
USPC ........................................................ 345/419
See application file for complete search history.

(56) References Cited

U.S. PATENT DOCUMENTS

| 4,742,464 A | 5/1988 | Duret et al. |
| 6,382,975 B1 | 5/2002 | Poirier |

(Continued)

FOREIGN PATENT DOCUMENTS

| DE | 102004035091 A1 | 2/2006 |
| DE | 102005011066 A1 | 9/2006 |

(Continued)

OTHER PUBLICATIONS

Leopoldseder et al. (Approximation of developable surfaces with cone spline surfaces, 1997).*

(Continued)

*Primary Examiner* — Maurice L McDowell, Jr.
*Assistant Examiner* — Kyle Zhai
(74) *Attorney, Agent, or Firm* — Novak Druce Connolly Bove + Quigg LLP (57) ABSTRACT

Method for modelling an individual dental prosthesis, which includes an abutment, wherein a first geometry is ascertained by a detection device, wherein an auxiliary element is affixed to at least one manipulation implant/implant, and a first data set is determined therefrom. A second data set describing a geometry having at least one manipulation implant/implant without an auxiliary element is ascertained. Using the second data set, which includes no data from auxiliary elements, or using the first and second data sets, a direction of insertion is determined by which a dental prosthesis part is to be pushed onto the abutment. A production method and a system for modelling an individual dental prosthesis and a computer-readable medium having instructions, which, when loaded into a computer, execute the methods A further method is provided for automatically determining a direction of insertion for a dental prosthesis part.

35 Claims, 4 Drawing Sheets

(51) Int. Cl.
*A61C 9/00* (2006.01)
*A61C 8/00* (2006.01)

(56) References Cited

U.S. PATENT DOCUMENTS

| | | | |
|---|---|---|---|
| 6,788,986 | B1 | 9/2004 | Traber et al. |
| 8,257,083 | B2 * | 9/2012 | Berckmans et al. .......... 433/213 |
| 2002/0037489 | A1 | 3/2002 | Jones et al. |
| 2003/0219148 | A1 | 11/2003 | Scharlack et al. |
| 2005/0214716 | A1 | 9/2005 | Weber et al. |
| 2006/0019219 | A1 | 1/2006 | Saliger et al. |
| 2006/0111806 | A1 * | 5/2006 | Kraemer et al. .............. 700/117 |
| 2006/0147872 | A1 * | 7/2006 | Andreiko ........................ 433/24 |

FOREIGN PATENT DOCUMENTS

| | | |
|---|---|---|
| EP | 1062916 A2 | 5/2000 |
| EP | 1062916 A2 | 12/2000 |
| EP | 1568335 A2 | 2/2005 |
| EP | 1618854 A1 | 6/2005 |
| EP | 1662414 A2 | 11/2005 |
| JP | H06-154252 | 6/1994 |
| JP | 2001-54525 | 2/2001 |
| JP | 2006-502817 | 1/2006 |
| WO | WO 2007/011909 A1 | 1/2007 |
| WO | WO 2007/081557 A1 | 7/2007 |

OTHER PUBLICATIONS

May 21, 2013 Office Action in corresponding JP 2010-543442 (with English Translation).
International Preliminary Report on Patentability dated Sep. 16, 2010.
Aug. 21, 2012 Office Action in corresponding JP Patent Application 2010-543442, with English translation.
Aug. 13, 2012 (approx.) Office Action in corresponding CN Patent Application 200980103079.8, with English translation.
International Search Report dated Jul. 30, 2009 in corresponding PCT/EP2009/000478.
German Search Report dated Oct. 2, 2008 in corresponding DE 10 2008 006 048.8.

* cited by examiner

METHOD FOR MODELING AN INDIVIDUAL DENTAL PROSTHESIS

FIELD OF INVENTION

The invention relates to methods for modelling an individual dental prosthesis, methods for producing an individual dental prosthesis and systems for modelling an individual dental prosthesis, as well as computer-readable media and a method for automatic determination of a direction of insertion for a dental prosthesis part.

BACKGROUND

From the state of the art, it is known to measure a residual tooth area after the dental preparation by means of optical scanning directly in the patient's mouth or by means of optical scanning of a model that represents the situation in the mouth of the patient. It is furthermore known to model models of dental prosthesis parts digitally, whereby scanned data of the residual tooth area are taken into consideration.

Furthermore, it is known, as given in EP 1 062 916 A2, to produce a working model of a jaw impression, in which, depending upon the dental prosthesis to be produced, one or more manipulation implants are worked in, whereby these manipulation implants describe the position of the implants in the jaw. Because the manipulation implants do not protrude or only barely protrude from the working model, an auxiliary element that protrudes from the working model is affixed to each manipulation implant. The auxiliary elements describe the deployment depth, longitudinal axis alignment and angular position of the manipulation implants in the working model. It should be possible to have additional data ascertained with the ascertained data of the geometry of the working model with affixed auxiliary bodies, whereby these data are required for the fully automatic production and for the determination of the direction of insertion of the additional elements of the individual dental prosthesis.

SUMMARY OF THE INVENTION

The object of the present invention is to provide a method for modelling an individual dental prosthesis, a method for producing an individual dental prosthesis and a system for modelling an individual dental prosthesis, so that one or more improved data sets are available during the modelling of the dental prosthesis, which leads to a well-producible dental prosthesis.

It is moreover the object of the present invention to provide a method for automatically determining a direction of insertion for a dental prosthesis part so that time savings result in the determination of the direction of insertion as compared to the determination of the direction of insertion by a user.

This object is solved with various methods, systems and a computer readable medium according to the invention.

In one method for modelling an individual dental prosthesis that comprises an abutment, at least one manipulation implant, which corresponds to an implant in the residual tooth area, is affixed in a model of a residual tooth area that is to be provided with the dental prosthesis.

An auxiliary element can be affixed to each manipulation implant in the model, whereby the auxiliary element, together with the manipulation implant, describes the position of the implant in the residual tooth area. A first three-dimensional geometry of the model with the at least one auxiliary element can be ascertained by means of a detection device, and a first data set can be determined therefrom, whereby this first data set describes the first three-dimensional geometry.

A second three-dimensional geometry of the model with the at least one manipulation implant but without, however, the auxiliary element, can be ascertained by means of a detection device, and a second data set can be determined therefrom, whereby this second data set describes the second three-dimensional geometry. The second geometry can also be ascertained before the ascertainment of the first geometry.

If the model of a residual tooth area is ascertained without affixed auxiliary elements, possible shadowing effects due to the auxiliary bodies can be avoided. If an auxiliary body is affixed to a manipulation implant, it can happen, depending on the position of the auxiliary body, whose position is also determined by the position of the manipulation implant, that certain areas, for example, a gap between teeth, cannot be ascertained by the detection device. This can be detrimental if, e.g., an outer shape of the abutment is to be specified, because then the corresponding shape cannot be defined. Without the affixed auxiliary element, the entire area, for example, of the gap between teeth, can be ascertained and an outer shape of the abutment can be correspondingly defined.

For example, the outer shape of the abutment can be defined using an existing distance to adjacent teeth that lie in the same and/or opposite jaw (upper or lower jaw) and/or using the shape or the axes of the adjacent teeth. Furthermore, outer shapes of common abutments can also be available as suggestions, for example, parameterized, and, for example, such a suggestion can be used for a definition of an outer shape of the abutment (to be produced). The available outer shapes of common abutments can be altered and/or processed, so that the resulting outer shape can be used, for example, for the abutment (to be produced). The outer shapes of common abutments can be classified according to various tooth types and/or various connection geometries of the abutments at an implant, as a result of which a simple and/or rapid selection of an outer shape of a common abutment can result as a suggestion for an abutment (to be produced).

Large auxiliary bodies are generally preferred for the auxiliary bodies, because with these, the geometric shape and position can be recognized with especially small errors. Such large auxiliary bodies in particular also generate large shadowing effects that are, however, particularly undesired.

With the use of the second data set, a direction of insertion can be determined by which a dental prosthesis part should be pushed onto the abutment. The direction of insertion of the dental prosthesis part can, for example, be conditional upon the outer shape of the abutment and/or upon adjacent teeth, so that the dental prosthesis part can be satisfactorily pushed into the target position. To be understood here as the outer shape of the abutment is the surface of the abutment that faces toward the dental prosthesis part to be affixed. The determination of the direction of insertion from the second data set can even take place before the ascertainment of the first data set, because the second data set can preferably be used during the determination of the direction of insertion by which a dental prosthesis part should be pushed onto the abutment, but the first data set is not used. The order of the ascertainment of the two data sets is also optional.

The outer shape of an abutment can, for example, be defined by including a previously ascertained direction of insertion, whereby it is not necessary for the abutment to be already partially or completely known or ascertained at the time of the determination of the direction of insertion.

The determination of the direction of insertion can, for example, be based upon various axes that are implicitly or explicitly comprised by the ascertained data set. This can, for example, be the axes of the adjacent teeth and/or the perpendicular to a surface that is given by the U-shape of the upper or lower jaw and/or by the equatorial surface of the adjacent teeth, whereby the equatorial surface can be specified by the largest horizontal circumference of a tooth. A further criterion can be that a closed tooth line is obtained.

The second data set is based upon the geometry of the model of the residual tooth area with at least one manipulation implant at which no auxiliary element is affixed. Shadowing effects due to the auxiliary elements can therefore be avoided and a direction of insertion of the dental prosthesis part can be determined, for example, with consideration given to the adjacent teeth.

By using the first data set and the second data set for determining a direction of insertion by which a dental prosthesis part can be pushed onto the abutment, the advantages contained in the information in the two data sets can be combined. By using the first data set, the position of the manipulation implant in the model of the residual tooth area and consequently the position of the implant in the residual tooth area of a patient can be determined precisely by the affixed auxiliary body, and by using the second data set, it can be guaranteed that all areas of the model of the residual tooth area are described in the data set and that it is not the case that certain areas of the model of the residual tooth area are covered by an auxiliary element, as, for example, can occur in the first data set.

The position of the manipulation implant can also influence the direction of insertion by which the dental prosthesis part can be pushed onto the abutment. The abutment that is comprised by the dental prosthesis part can be affixed onto the manipulation implant. It can moreover be provided that the abutment is connected to the manipulation implant, for example, by means of a screw. In order to guarantee this, a certain shape of the abutment can be provided that allows a screw channel to be provided in such a way that a screw can be connected to the manipulation implant through the abutment in a stable manner. For this purpose, the abutment can have a necessary material thickness in certain areas, whereby this material thickness guarantees such a stable connection, whereby the outer shape of the abutment, which can also determine the material thickness, can in turn be selected in such a way that the abutment can easily be introduced into the model of the residual tooth area, for example, a gap between teeth. The outer shape of the abutment and the surroundings of the residual tooth area around the abutment, i.e., for example, adjacent teeth of a gap between teeth, can be determining for the direction of insertion of the dental prosthesis part onto the abutment.

By using the second data set, possible shadowing effects due to the auxiliary body can be avoided, as already described above. Without the affixed auxiliary element, the entire area of the, for example, gap between teeth, can be ascertained and accordingly to an outer shape of the abutment can be determined.

The dental prosthesis part can be or comprise, for example, an overlay, an onlay, a cap, a crown, a primary crown, a secondary crown, a bridge or a framework.

The method can additionally comprise a step of determining the abutment data that define the abutment. The step of determining the abutment data can comprise the determination of a connection geometry of the abutment to the implant in the residual tooth area. In the event of a plurality of implants that are provided in order to attach, for example, a bridge, it is advantageous if the implant is rotationally symmetrical in its upper shape onto which the abutment is to be affixed, in order not to geometrically overdetermine the dental restoration. In addition or instead, the abutment can be rotationally symmetrical in its outer shape onto which the dental prosthesis part is to be affixed.

If, however, an implant is provided onto which only a single dental prosthesis part, such as a crown or the like, is to be affixed, it is advantageous if the implant is not rotationally symmetrical in the corresponding area in order to prevent twisting of the dental prosthesis part. It is correspondingly then advantageous if the corresponding abutment in the corresponding part that comes into contact with the implant is also not rotationally symmetrical. It is furthermore also advantageous, however, if the abutment is not rotationally symmetrical in its outer shape that comes into contact with the dental prosthesis part.

For specifying the connection geometry of the abutment to the implant, information previously stored in the computer and regarding the needed/desired geometry of the abutment in the connection area and/or regarding the geometry of the implant in the connection area can be used. Previously stored information can also be used for creating a screw channel (see below).

Using the first and/or second data set, a direction can be determined by which the abutment can be affixed onto the implant. This direction can be specified by the adjacent teeth as well as by the position of the implant. The direction by which the abutment can be affixed onto the implant can be different than the direction of insertion of the dental prosthesis part onto the abutment, even for single-tooth restorations. Said direction and the direction of insertion can, however, also be the same.

A screw channel can be modelled in the abutment, whereby the longitudinal axis of the screw channel corresponds to an axis of the implant in the residual tooth area, whereby preferably the first data set can be also or exclusively accessed for this. The second data set can optionally also be used.

Furthermore, suitable software can be used to check whether or not a screw can be inserted into the screw channel of the abutment, if the abutment is affixed onto the implant in the residual tooth area or onto the manipulation implant in the model. The check can, for example, also be made by using the second data set.

The check of the insertability of the screw into the screw channel can guarantee the use of the abutment, because, for example, the screw channel otherwise could be covered by an adjacent tooth, in which case it would therefore not be possible to attach the abutment to the implant by using the screw. A new abutment would have to be produced in this case. Where necessary, the check can allow a new abutment to be designed before it is produced.

An outer shape of the abutment can be determined by means of the second data set. The second data set describes the geometry of the model with the at least one manipulation implant onto which there is no auxiliary element affixed. Due to the fact that no auxiliary element is used, there are no problems with shadowing effects during the ascertainment of, for example, an existing gap between teeth, in which the manipulation implant is located. The outer shape of the abutment can be correspondingly determined, so that, for example, a dental prosthesis part to be attached has sufficient room in the gap between teeth.

The affixability of the abutment to the implant in the residual tooth area can be checked. As a result, it can be guaranteed that, for example, both the direction by which the abutment should be affixed onto the implant and also the outer shape of the abutment are in harmony with the conditions of the residual tooth area. The check of the affixability of the abutment can, for example, also be made in the model of the residual tooth area.

An inner shape of the dental prosthesis part can be determined with consideration given to the outer shape of the abutment. To be understood here as the inner shape of the dental prosthesis part is the surface of the dental prosthesis part that faces toward the abutment. In determining the inner shape of the dental prosthesis part, areas can also be provided for the placement of cement or adhesive, whereby cement or adhesive can serve as a means of connecting the abutment and dental prosthesis part.

In a method for producing an individual dental prosthesis that comprises an abutment, the production of the abutment and/or of the dental prosthesis part can take place by means of milling from a pre-manufactured blank, or from any shaped blank, such as a plate. During the milling, a steel or diamond milling cutter can, for example, be used.

The blanks can be or can comprise sintered-through, pre-sintered, (already sintered, but not yet sintered through) and unsintered (green bodies) ceramics or one of the materials listed in the following.

Metal, ceramic, glass or plastic can be used as materials for the abutment and/or the dental prosthesis part. Plastic or (glass-)fibre reinforced plastic, for example, can be used thereby, as well as metal or metal alloys, such as, for example, cobalt alloy, chrome-cobalt alloy, titanium or titanium alloy, gold or gold alloy. Moreover, ceramics, such as, for example, zirconium-oxide, yttrium-stabilized zirconium-oxide or aluminium-oxide can be used.

In a system for modelling an individual dental prosthesis that comprises an abutment, means are provided in order to ascertain a first data set that describes a first three-dimensional geometry, whereby this geometry comprises a model of a residual tooth area that is to be provided with a dental prosthesis as well as at least one manipulation implant onto which an auxiliary element is affixed, and in order to ascertain a second data set that describes a second three-dimensional geometry, whereby this geometry comprises the model of the residual tooth area that is to be provided with a dental prosthesis as well as at least one manipulation implant onto which no auxiliary element is affixed. By using the second data set, however preferably without using the first data set, or by using the first data set and the second data set, a direction of insertion can be determined by which a dental prosthesis part can be pushed onto the abutment. The device can consequently be formed in such a way that a direction of insertion can even be determined from a data set that comprises no data regarding the auxiliary bodies.

The ascertained data sets can additionally be stored, further processed and/or sent by means of remote data transmission.

The invention also relates to a computer-readable data medium that comprises instructions that, when loaded into a computer, execute one of the methods described above or further below.

In a method for modelling an individual dental prosthesis that comprises an abutment, an auxiliary element is affixed to one, several or all implants that are located in a residual tooth area of a patient who is to be provided with a dental prosthesis, whereby this auxiliary element, together with the implant, describes the position of the implant in the residual tooth area. A first three-dimensional geometry of the residual tooth area with the at least one auxiliary element can be ascertained by means of a detection device, and a first data set can be determined therefrom, whereby this first data set describes the first three-dimensional geometry.

A second three-dimensional geometry of the residual tooth area with the at least one implant but without, however, the auxiliary element, can be ascertained by means of a detection device, and a second data set can be determined therefrom, whereby this second data set describes the second three-dimensional geometry. The second geometry can also be ascertained before the ascertainment of the first geometry.

The method steps described above or below can correspondingly be performed with these ascertained data sets, whereby it must be observed that instead of the model of the residual tooth area and manipulation implants, the residual tooth area itself and implants are used.

The invention relates moreover to a method for automatically determining a direction of insertion for a dental prosthesis part.

Three points that stand out the farthest from the jaw can be selected from teeth or from gum elevations that are located in the dental arch in which a residual tooth area is located that is to be provided with a dental prosthesis. A plane can be laid through these three points, whose perpendicular can specify the direction of insertion. A dental arch here is understood to be the upper jaw or the lower jaw of a patient.

A dental arch can be divided into a incisor area and into the two molar areas, whereby a point standing out the farthest from the jaw can be selected in each of the three areas and a plane can be laid through these three points, whereby the perpendicular of this plane can specify the direction of insertion. A division into the three areas can also be made if not all teeth are still present, or if no teeth are still present, whereby then the areas in which incisors and/or molars should be present can be used for the division.

The areas of the canine teeth can be included in the area of the incisors and/or in the respective area of the molars. It is, however, also possible to provide separate areas for the area of the canine teeth and/or not to take into consideration the canine teeth or the areas of the canine teeth.

Three points standing out from the jaw can be selected from the teeth and from gum elevations that are located in a dental arch, whereby:

a) the point standing out the farthest from the jaw is selected as a first point;

b) the point standing out the next farthest from the jaw is selected as a second point, if the second point has a minimum distance to the first point, whereby the minimum distance amounts to 1 cm, 1.5 cm, 2 cm, 2.5 cm or more;

c) if the distance between the first and the second point is less than the minimum distance, the second point is rejected and steps b) and c) are repeated until a second point has been selected, whereby in each of the steps b) and c) the point is used that stands out a smaller distance from the jaw than the previously used points;

d) if a second point has been selected according to b), a third point is selected if the third point is a minimum distance apart from both the first point and the second point, whereby a point that stands out a smaller distance from the jaw than the previously used points is used as the third point;

e) if the distance between the third and the first and/or the third and the second point is less than the minimum distance, the third point is rejected and steps d) and e) are repeated until a third point has been selected, whereby in each of the steps d) and e) the point is used that stands out a smaller distance from the jaw than the previously used points;

f) when three points have been selected, a plane is laid through these three points, whereby the perpendicular to this plane specifies the direction of insertion.

Three or more tangents can be laid on the edges of a ground tooth and/or the edges of an abutment that is located in a residual tooth area that is to be provided with a dental prosthesis, whereby a cone envelope can be specified by these tangents around the ground tooth and/or the abutment, whereby the aperture angle of the cone can define an angular range for the direction of insertion.

An additional ground tooth and/or an additional abutment can be located in the residual tooth area, whereby the additional ground tooth and/or the additional abutment is to be provided with an additional or the same dental prosthesis, whereby three or more additional tangents can be laid on the additional ground tooth and/or the additional abutment, by means of which tangents an additional cone envelope can be specified around the additional ground tooth and/or the additional abutment, whereby an angular range can result for the direction of insertion from an intersection of the two aperture angles of the two cones.

A direction of an axis of a ground tooth and/or of an abutment, together with an implant, which ground tooth and/or abutment is located in a residual tooth area and which is to be provided with the dental prosthesis, can define the direction of insertion.

The direction of the axis of the ground tooth and/or of the abutment together with the implant can be determined from the volume data of the ground tooth and/or of the abutment together with the implant.

The direction of the axis can correspond to the direction of the longest line within the ground tooth and/or the abutment together with the implant, and/or the direction of the axis can correspond to a projection direction in which the volume of the ground tooth and/or the abutment together with the implant has a smallest possible area when projected onto a plane.

The direction of the axis of the ground tooth can correspond to a perpendicular through an equatorial surface of the ground tooth, whereby the equatorial surface can be defined by a largest horizontal circumference of the ground tooth.

An equatorial line of the ground tooth can be fit with a circle, an ellipse and/or a polygon, and the direction of the axis can correspond to the perpendicular to the circular, elliptical and/or polygonal plane, whereby the equatorial line can be given by a largest horizontal circumference of the ground tooth.

The direction of the axis of the ground tooth can be defined by a perpendicular through an area that is given by a preparation line of the ground tooth.

A preparation line of a ground tooth can be fit with a circle, an ellipse and/or a polygon, and the direction of the axis of the ground tooth can correspond to the perpendicular to the circular, elliptical and/or polygonal plane.

The direction of insertion of the dental prosthesis part can be defined with consideration of side surfaces of adjacent teeth that join to a residual tooth area that is to be provided with the dental prosthesis, whereby only those side surfaces are considered that face the dental prosthesis.

A user can select, modify and/or save the automatically determined direction of insertion, and/or select and/or save the modified direction of insertion.

BRIEF DESCRIPTION OF THE DRAWINGS

Embodiments of the invention will be explained using the accompanying figures. Shown are.

DETAILED DESCRIPTION

Figure 1:
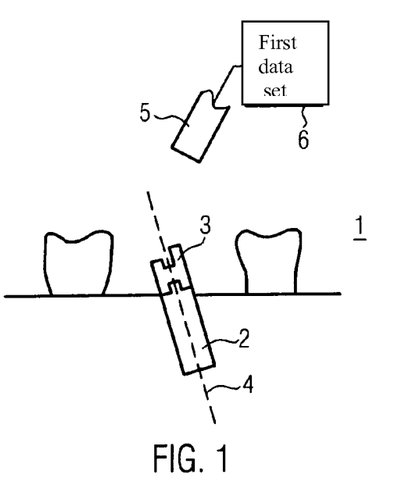
FIG. 1: Model of a residual tooth area with manipulation implant and with auxiliary element.

FIG. 1 shows a model of a residual tooth area 1 that comprises a plurality of teeth along with a manipulation implant 2 with an affixed auxiliary element 3. The manipulation implant 2 can take on the position relative to model 1 that corresponds to the position of a corresponding implant 10 in the jaw of a patient. The longitudinal axis 4 of the manipulation implant can correspond to the orientation of the longitudinal axis 11 of the implant in the patient's mouth. The auxiliary element 3 can, together with the manipulation implant 2, describe the position of the implant 10 in the jaw area.

A geometry of this model of the residual tooth area 1 can be ascertained with a detection device 5, for example, with a scanner. A data set 6 of this geometry can additionally be passed on, processed or stored.

The auxiliary element 3 can have a characteristic shape that can be recognized well in the data set 6, so that it is possible to determine the position of the manipulation implant 2 and/or the implant 10 from the recognized position of the auxiliary element 3.

Figure 2:
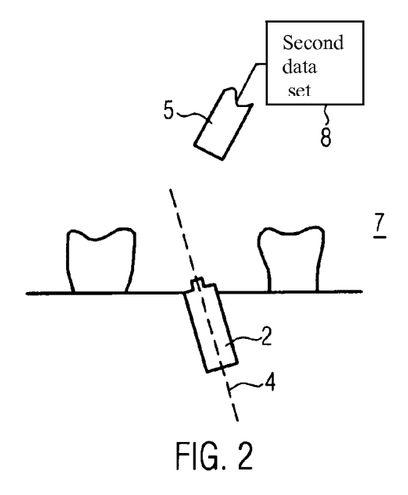
FIG. 2: Model of a residual tooth area with manipulation implant without auxiliary element.

FIG. 2 shows a model of the residual tooth area 7, whereby no auxiliary element is, however, affixed onto the manipulation implant 2. Here again a data set 8 that describes the geometry of this model 7 can be ascertained with the detection device 5, whereby the data set 8 can be passed on, processed or stored. The position of the upper end of a manipulation implant can be roughly determined from this data set 8. As a rule, the information is not sufficient for exactly determining the precise position of the manipulation implant 2, but the position of the upper end can be determined with sufficient precision. With, for example, this information, as well as, for example, with the data on the shape of the residual tooth area, such as arrangement, and/or size of the adjacent teeth, the direction of insertion, for example, can be defined by which a dental prosthesis part can be pushed onto an abutment, whereby the abutment can be affixed onto the implant.

Figure 3:
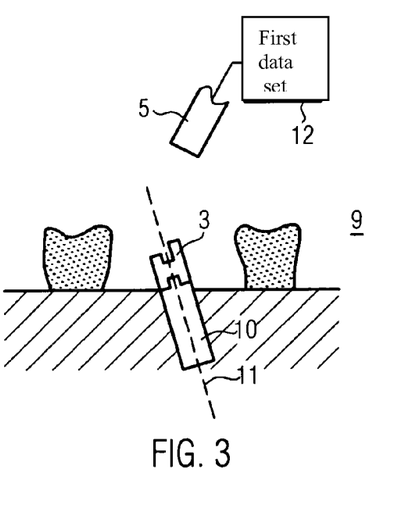
FIG. 3: Residual tooth area of the patient, with implant and auxiliary element.

FIG. 3 shows the residual tooth area 9 of a patient, whereby the area in the case shown comprises a plurality of teeth as well as an implant 10 onto which an auxiliary element 3 is affixed. The residual tooth area 9 can be ascertained by means of a detection unit 5, whereby this detection unit can be the same as the detection unit for ascertaining the models; the two detection units can also be different, however. The determined data set 12 can be passed on, processed and/or stored. The implant 10 in the jaw of the patient can have a longitudinal axis 11. The position of the implant can be roughly determined from the upper end of the implant.

Figure 4:
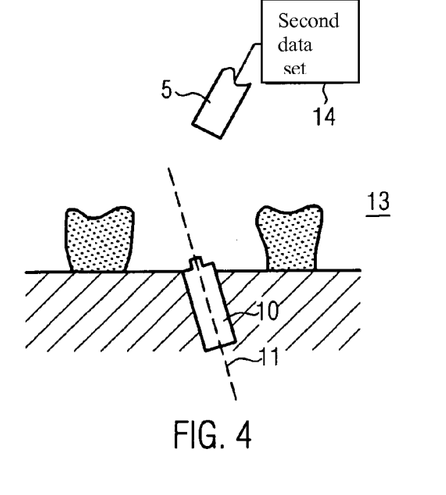
FIG. 4: Residual tooth area of the patient, with implant without auxiliary element.

FIG. 4 shows a residual tooth area 13 of the patient, whereby no auxiliary element is affixed onto the implant 10. The geometry of this residual tooth area 13 can be ascertained with a detection unit 5, and the data set 14 obtained in this way can be passed on, processed and/or stored.

Figures 5, 6, 7:
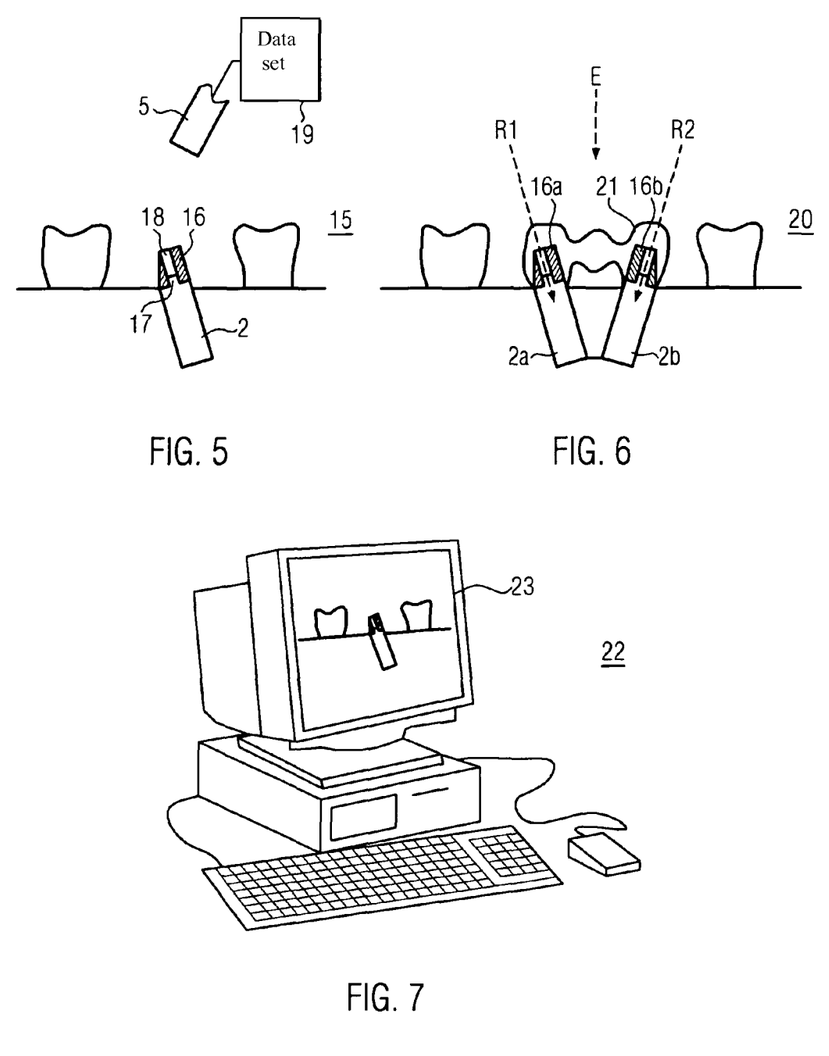
FIG. 5: Model of a residual tooth area with manipulation implant and affixed abutment.
FIG. 6: Model of a residual tooth area with two manipulation implants, two abutments and one dental prosthesis part.
FIG. 7: System for modelling an individual dental prosthesis.

FIG. 5 shows a model of a residual tooth area 15 onto the manipulation implant 2 of which an abutment 16 is affixed. The abutment 16 can have a screw channel 18 in order to connect the abutment 16 and (manipulation) implant 2, 10, for example, by means of a screw. The longitudinal axis of the screw channel can correspond to the axis of the manipulation implant 4 and the axis of the implant 11, so that the abutment 16 and the manipulation implant 2 and/or the abutment 16 and implant 10 can be connected to each other without tensions that can, for example, be caused by a twisted screw. The longitudinal axis of the screw channel and the axis of the implant 11 can also, however, be slanted with respect to each other or can be skewed with respect to each other. Adapters can be inserted between the implant and abutment for this purpose.

An outer shape of an abutment 16 can be determined by using the data set 8, which describes the geometry of the corresponding model without affixed auxiliary elements (see FIG. 2). The possible outer shape of an abutment 16 can be restricted by the arrangement of adjacent teeth, a direction by which the abutment 16 is to be affixed onto the manipulation implant 2 and/or implant 10 or the possibility of the insertion of a screw into the screw channel 18 and/or its attachment in the manipulation implant 2 and/or implant 10. The outer shape of an abutment 16 can also be necessitated by one or more characteristics of a dental prosthesis part that is to be pushed on. Such characteristics can, for example, be the direction of insertion of the dental prosthesis part, minimal thickness of the material of the dental prosthesis part or existing undercuts of the dental prosthesis part.

Manipulation implant 2 and implant 10 as well as the abutment 16 can have connection geometries 7 at their ends that guarantee that the parts can be positioned appropriately against one another and, for example, a twisting of the abutment 16 on the manipulation implant 2 and/or implant 10 can be prevented.

FIG. 6 shows a model of a residual tooth area 20 with two manipulation implants 2a, 2b and with affixed abutments 16a, 16b. A three-section bridge 21 with a pontic is affixed onto the abutments 16a, 16b. The manipulation implants 2a, 2b have different alignments. The outer shape of the abutments 16a, 16b can be defined with consideration given to the alignment and position of the manipulation implants 2a, 2b and/or the corresponding implants in such a way that the two directions R1, R2 that are given by the longitudinal axes of the manipulation implants and/or of the implants are transformed into a single direction of insertion. As a result, it is possible to push a multi-sectional dental prosthesis part 21 onto the corresponding abutments 16a, 16b by a single direction of insertion E. The dental prosthesis part 21 can, for example, also be given a facing in order to correspond, in terms of the colour and shape, to the teeth in the mouth of a patient.

FIG. 7 shows a system 22 for modelling an individual dental prosthesis. Using a computer, one or more data sets 6, 8, 12, 14, 19 can be loaded in, such as, for example, the data sets that describe the geometry of the models of a residual tooth area with and without auxiliary elements. The data set that describes the residual tooth area of the patient can moreover be loaded in. The data sets can be processed, and corresponding views of a model and/or of a residual tooth area can, for example, be depicted on a monitor 23. It is possible to edit the data. At the same time, editing steps can be selected and/or carried out by a user by means of a keyboard, a mouse or also by audio signals. The editing steps can also be carried out automatically by using predefined characteristics, such as, for example, materials to be used or specified geometries. The edited data sets can be stored and/or sent, so that the production of an abutment and/or a dental prosthesis part can take place at the location of the editing or the production can, for example, take place in a manufacturing centre.

A method for modelling an abutment 16 can consequently proceed as follows: The model 1, 7 is scanned once with and once without auxiliary elements 3 (see FIGS. 1 and 2), whereby the order is optional. The direction of insertion E can be determined from the data set 8, 14 without auxiliary elements 3, for example, as described above. For this purpose, the data can, for example, be depicted simply, together with a possible direction of insertion E that is, for example, depicted as a line. The data can also be depicted as a surface from the point of view of the direction of insertion E, or consequently with a view onto the model surface along the direction of insertion. The direction of insertion E or the view onto the data is then modified by means of operator inputs, until the operator agrees with the selected direction of insertion E.

The method for modelling an abutment 16 can, however, also be carried out with the use of the data sets 12, 14, which comprise the three-dimensional geometry of the residual tooth area with implant and with affixed auxiliary element or the three-dimensional geometry of the residual tooth area with implant but without auxiliary element. The direction of insertion E can also be determined with the use of these data sets 12, 14.

Then the outer area of the abutment 16 can be modelled with or without the help of this direction of insertion E. A cone envelope stub around the direction of the direction of insertion E, for example, is suggested for this. Such a suggestion can still be modified with suitable means in the data model by the user. The model of the abutment 16 can here be modelled in such a way, with consideration of the data set without auxiliary bodies, that the abutment matches the other adjacent teeth or generally matches the residual tooth area. In this connection, the approximate information regarding the position of the upper end of the (manipulation) implant 2, 10 that was acquired from the data set 8, 14 without auxiliary body 3 is used in order to form the abutment 16 in such a way that it is possible also to attach it to the (manipulation) implant 2, 10.

To complete the data set that describes the abutment 16, the underside and the screw channel 18 are now still to be modelled. For this purpose, for example, the already generated data set of the abutment 16 can be superimposed into a representation of the dataset with auxiliary bodies 3. For example, the relative position of the planned abutment 16 compared to the adjacent teeth or to the residual tooth area can be used for this, because these data are equally available in both data sets 6, 8, 12, 14 (with and without auxiliary bodies). The exact positions of the (manipulation) implants 2, 10 are known from the data set 6, 12 with auxiliary bodies 3, so that the screw channel 18 is preferably formed along the implant axes and the information about the exact position of the (manipulation) implant 2, 10 is used in order to form the underside of the abutment 16 correspondingly. This allows an abutment 16 to be created whose outer shape can be optimally formed, because no disrupting auxiliary bodies cause shadowing effects in the corresponding data set 8, 14, and with which on the other hand the underside can be modelled with the necessary precision, because a data set with auxiliary bodies is available.

The data set of an abutment modelled in this way can then be sent to a production station or a production centre, for example, via remote data transmission, for the production of the abutment.

Figure 8:
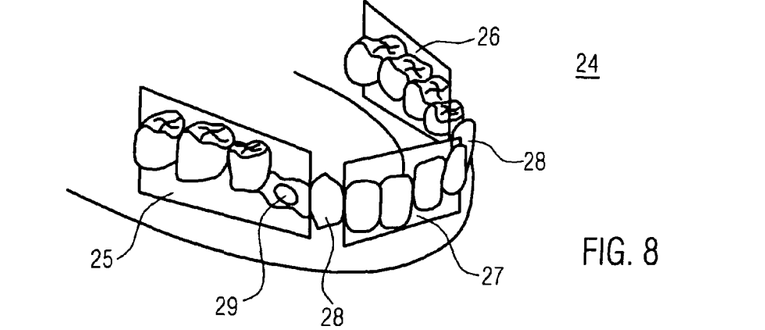
FIG. 8: Schematic representation of a dental arch with a gap between teeth.

FIG. 8 shows a schematic representation of a dental arch with a gap between teeth 29. The dental arch 24 can be divided into three areas, for example, as shown here, into two areas of molars 25, 26 and one incisor area 27. The canine teeth 28 here are not assigned to any of the three areas, but can, for example, be assigned to the incisor area or to the corresponding areas of the molars. It is also possible to assign separate areas to the canine teeth. An implant and an abutment can be placed or can have been placed in the gap between teeth, whereby a dental prosthesis part can then be affixed onto them. A possible direction of insertion for the dental prosthesis part can be determined in that three points standing out from the jaw are selected, and then a plane is laid through these points, whereby the perpendicular to the plane can define the possible direction of insertion.

For a selection of the points, it can be provided that:
One point from each one of the three shown areas can be selected, whereby the respective point can be the one that stands out the farthest from the jaw. The points that stand out the farthest from the jaw can be given by the tip of the tooth or also by gum elevations if there are no more teeth in the jaw or in a jaw area.
There is a minimum distance between all pairs of the three points.

Figure 9:
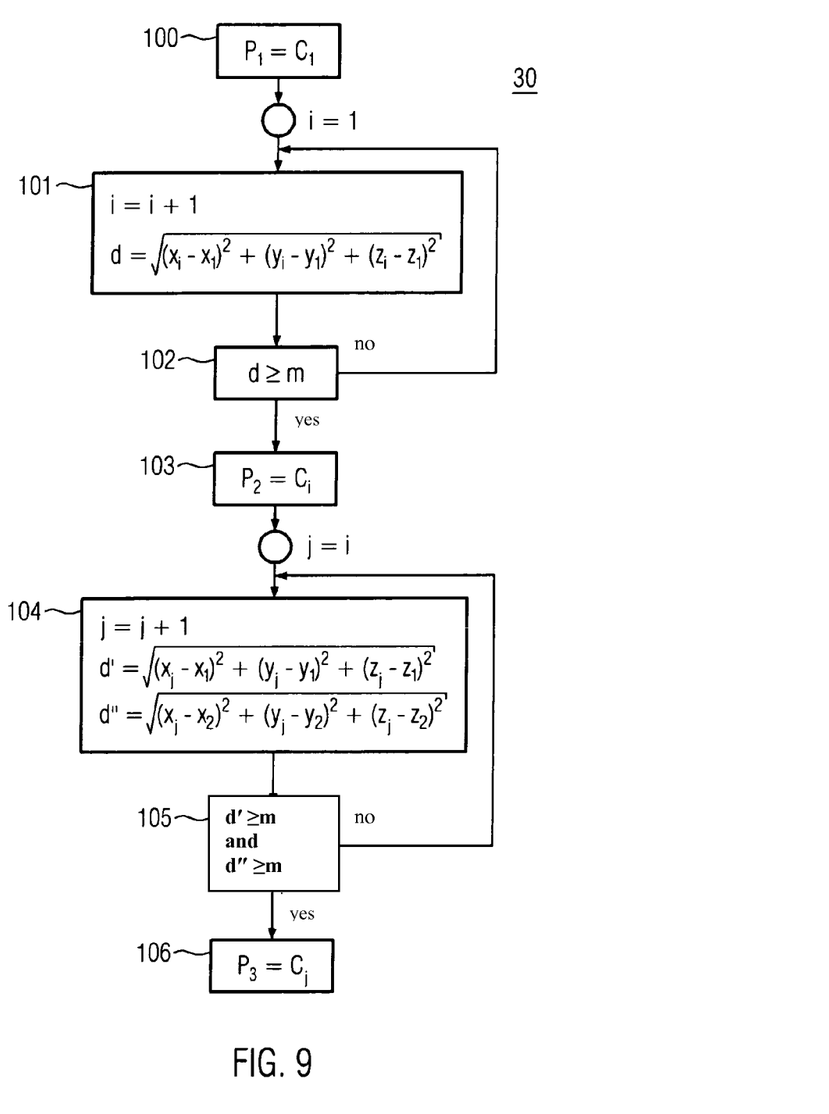
FIG. 9: Flowchart for the selection of points standing out from the jaw.

FIG. 9 shows a flowchart for the selection of points standing out from the jaw. A database (not shown) can be available that contains the coordinates of such points that stand out from the jaw. For example, the points can be sorted in such a way that the points $C_i$ with a higher index i stand out less from the jaw than such points $C_i$ with a higher index value i. In step 100, the point $C_{i=1}$ that stands out the farthest from the jaw is selected as the first point $P_1$.

In step 101, the distance d between the first point $P_1$ and the point $C_{i=2}$ is determined for the next point $C_{i=2}$. In step 102, a check is made to see whether or not the distance d between the first point $P_1$ and the point $C_{i=2}$ is greater than or equal to a minimum distance m. The minimum distance can, for example, be 1 cm, 1.5 cm, 2 cm, 2.5 cm or more. The minimum distance can, however, also be smaller.

If d is greater than or equal to m, in step 103 the point $C_{i=2}$ is selected as the second point $P_2$. If the distance d is less than the minimum distance m, steps 101 and 102 are repeated until a point $C_i$ is found for which the distance d is greater than or equal to the minimum distance m. In the event that no such point is found, an automatic remark can be made. The remark can, for example, include that no second point could be selected and correspondingly the selection of points had to be ended.

If a point $C_i$ was assigned to the second point $P_2$ in step 103, in step 104 the distance d' to the first point $P_1$ and the distance d" to the second point $P_2$ is calculated for the next point $C_{j=i+1}$. In step 105, a check is made of whether or not the distances d' and d" are greater than or equal to the minimum distance m.

If they are, in step 106 the point $C_j$ is selected as the third point $P_3$. If the distances d' and/or d" are less than the minimum distance m, steps 104 and 105 are repeated until a point $C_j$ is found for which the distances d' and d" are greater than or equal to the minimum distance m. In the event that no such point is found, an automatic remark can be made. The remark can, for example, include that no third point could be selected and correspondingly the selection of points had to be ended.

Figure 10:
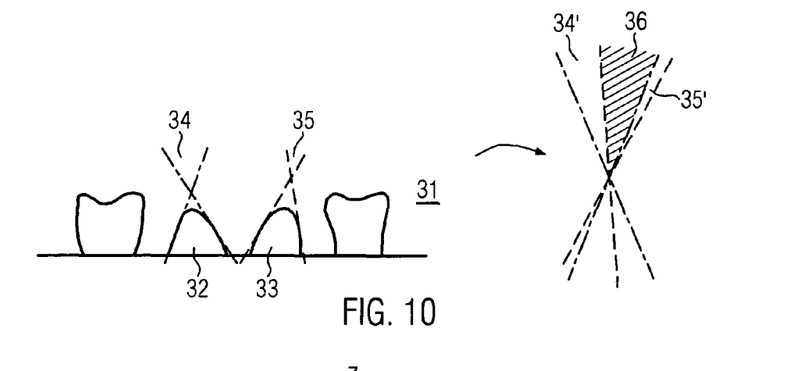
FIG. 10: Determination of the direction of insertion from the intersection of aperture angles of cones.

FIG. 10 schematically shows the determination of a direction of insertion for a dental prosthesis part on two ground teeth 32, 33, whereby the intersection 36 of two aperture angles of cones 34, 34', 35, 35' is taken into consideration for the direction of insertion. In order to specify a cone around a ground tooth 32, 33, three or more tangents can be laid on edges of the ground tooth in order to define a cone envelope that surrounds the ground tooth. If there are two ground teeth, there can correspondingly result two cone envelopes with different aperture angles and/or different directions of the cone axes. A direction of insertion for the dental prosthesis part can then result from the intersection 36 of the two aperture angles 34, 34', 35, 35'.

A cone envelope can, for example, also be laid around an abutment, whereby the aperture angle of the cone can specify a direction of insertion for a dental prosthesis part. If there is a plurality of abutments and/or if there is a combination of one and/or more abutments and/or of one and/or more ground teeth, the direction of insertion of the dental prosthesis part can be determined from the intersection of the corresponding aperture angles of the cones.

Figure 11:
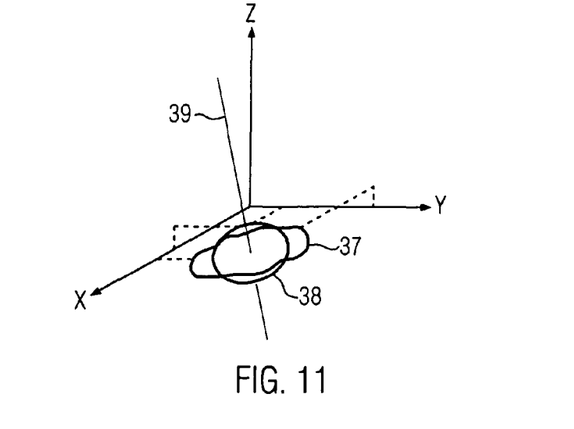
FIG. 11: Schematic representation of an equatorial line of a tooth with fitted circle.

A direction of insertion of a dental prosthesis part can, for example, be defined by the direction of an axis of a ground tooth. The direction of the axis of the ground tooth thereby can be given by the perpendicular to an equatorial surface of the ground tooth, whereby the equatorial surface is defined by the line of the largest, approximately horizontal circumference of the ground tooth. The equatorial line and correspondingly the equatorial surface will generally not run in a plane, but will instead, for example, have a wavy shape that describes the outer structure of the ground tooth.

FIG. 11 shows an equatorial line 37 of a tooth together with a circular curve 38 fit onto the equatorial line. The fit of the circular curve results in a circular plane that approximately describes the course of the equatorial line and that runs in a plane. The perpendicular 39 to the circular plane can then be used as a possible direction of insertion for a dental prosthesis part.

The invention claimed is:

1. Method for modelling an individual dental prosthesis that comprises an abutment, with the steps comprising:
   a) in a model of a residual tooth area to be provided with the dental prosthesis, at least one manipulation implant is affixed that corresponds to an implant in the residual tooth area;
   b) in the model, an auxiliary element is affixed onto one, several or each manipulation implant, wherein the auxiliary element, together with the manipulation implant, describes the position of the implant in the residual tooth area;
   c) a first three-dimensional geometry of the model with the at least one auxiliary element is ascertained by scanning with a detection device, and a first data set is determined therefrom, wherein this first data set describes the first three-dimensional geometry;
   d) a second three-dimensional geometry of the model with the at least one manipulation implant but without, however, the auxiliary element, is ascertained by scanning with the detection device, and a second data set is determined therefrom, wherein this second data set describes the second three-dimensional geometry, and
   e) by using the second data set or by using the first data set and the second data set, a direction of insertion is determined by which the dental prosthesis part is to be pushed onto the abutment, including determining with the first data set the position of the manipulation implant in the model of the residual tooth area, wherein consequently the position of the implant in the residual tooth area can be determined precisely by the affixed auxiliary element, and determining with the second data set that all areas of the model of the residual tooth area are described.

2. Method according to claim 1, wherein the dental prosthesis part comprises an overlay, onlay, cap, crown, primary crown, secondary crown, bridge or framework.

3. Method according to claim 1 further comprising the step f) for determining the abutment data that define the abutment.

4. Method according to claim 3, wherein the step of determining the abutment data comprises the determination of a connection geometry of the abutment at the implant in the residual tooth area and/or at the manipulation implant in the model.

5. Method according to claim 1, wherein a direction by which the abutment is affixed to the implant and/or the manipulation implant in the model is determined by using the first data set.

6. Method according to claim 1, wherein a screw channel is modelled in the abutment, wherein the longitudinal axis of the screw channel corresponds to an axis of the implant in the residual tooth area and/or that of the manipulation implant in the model.

7. Method according to claim 6, further comprising a check of whether or not a screw is insertable into the screw channel of the abutment, if the abutment is affixed onto the implant in the residual tooth area and/or onto the manipulation implant in the model.

8. Method according to claim 1, wherein an outer shape of the abutment is determined by using the second data set, wherein the outer shape of the abutment is restricted by at least one of an arrangement of adjacent teeth, a direction by which the abutment is to be affixed onto the implant, and attachment of the abutment in the implant.

9. Method according to claim 1, wherein affixability of the abutment onto the implant in the residual tooth area and/or onto the manipulation implant in the model is checked.

10. Method according to claim 1, wherein an inner shape of the dental prosthesis part is determined by the outer shape of the abutment.

11. Method according to claim 1, further comprising production of an individual dental prosthesis that comprises an abutment-utilizing the model of the residual tooth area.

12. Method according to claim 11, wherein the production of the abutment and/or the dental prosthesis part is done by milling from a pre-manufactured blank and/or from any shaped blank.

13. Method according to claim 12, wherein the blank comprises an unsintered, pre-sintered, or sintered-through ceramic blank, a metal blank or a plastic blank.

14. Method according to claim 11, wherein metal, ceramic, glass or plastic is used as materials for the abutment and/or the dental prosthesis part.

15. System including a processor and a non-transitory computer-readable medium with instructions that when loaded into the processor execute a method according to claim 11.

16. System including a processor and a non-transitory computer-readable medium with instructions that when loaded into the processor execute a method according to claim 1.

17. Method according to claim 1, further comprising production of an individual dental prosthesis part that comprises an abutment utilizing the model of the residual tooth area.

18. Method according to claim 17, wherein the production of the abutment and/or of the dental prosthesis part takes place by milling from a pre-manufactured blank and/or from a shaped blank with any shape.

19. Method according to claim 18, wherein the blank comprises an unsintered, pre-sintered or sintered-through ceramic blank, a metal blank or a plastic blank.

20. Method according to claim 17, wherein metal, ceramic, glass or plastic is used as materials for the abutment and/or the dental prosthesis part.

21. System for modelling an individual dental prosthesis that comprises an abutment the system comprising a detection device that ascertains a first data set and a second data set and a processor that determines a direction of insertion by which a dental prosthesis part is to be pushed onto the abutment, wherein:
  the first data set describes a first three-dimensional geometry, wherein this first geometry comprises a model of a residual tooth area that is to be provided with a dental prosthesis, as well as at least one manipulation implant onto which an auxiliary element is affixed, and
  the second data set describes a second three-dimensional geometry, wherein this second geometry comprises the model of the residual tooth area that is to be provided with a dental prosthesis, as well as at least one manipulation implant without an auxiliary element affixed onto it,
  and further comprising
  non-transitory computer readable medium with instructions that when loaded into the processor execute a method wherein,
  by using the second data set or by using the first data set and the second data set, the direction of insertion is determined by which the dental prosthesis part is to be pushed onto the abutment, including determining with the first data set the position of the manipulation implant in the model of the residual tooth area, wherein consequently the position of the implant in the residual tooth area can be determined precisely by the affixed auxiliary element, and determining with the second data set that all areas of the model of the residual tooth area are described.

22. Method according to claim 21, wherein, the determining step includes determining the direction of insertion as defined by side surfaces of adjacent teeth that join to a residual tooth area that is to be provided with the dental prosthesis, wherein the side surfaces are only those side surfaces that face the dental prosthesis.

23. Method for modelling an individual dental prosthesis that comprises an abutment, with the steps comprising:
  a) an auxiliary element is affixed to one, several or each implant in a residual tooth area of a patient who is to be provided with a dental prosthesis, wherein this auxiliary element, together with the implant, describes the position of the implant in the residual tooth area;
  b) a first three-dimensional geometry of the residual tooth area with the at least one auxiliary element is ascertained by scanning with a detection device, and a first data set is determined therefrom, wherein this first data set describes the first three-dimensional geometry;
  c) a second three-dimensional geometry of the residual tooth area with the at least one implant but without, however, the auxiliary element, is ascertained by scanning with the detection device, and a second data set is determined therefrom, wherein this second data set describes the second three-dimensional geometry, and d) by using the second data set or by using the first data set and the second data set, a direction of insertion can be determined by which a dental prosthesis part is to be pushed onto the abutment, including determining with the first data set the position of the manipulation implant in the model of the residual tooth area, wherein consequently the position of the implant in the residual tooth area can be determined precisely by the affixed auxiliary element, and determining with the second data set that all areas of the model of the residual tooth area are described.

24. Method according to claim 23, wherein the dental prosthesis part comprises an overlay, onlay, cap, crown, primary crown, secondary crown, bridge or framework.

25. Method according to claim 23, further comprising the step e) for determining the abutment data that define the abutment.

26. Method according to claim 25, wherein the step of determining the abutment data comprises the determination of a connection geometry of the abutment at the implant in the residual tooth area.

27. Method according to claim 23, wherein a direction by which the abutment is affixed onto the implant is determined by using the first data set.

28. Method according to claim 23, wherein a screw channel is modelled in the abutment, wherein the longitudinal axis of the screw channel corresponds to an axis of the implant in the residual tooth area.

29. Method according to claim 28, further comprising a check of whether or not a screw is insertable into the screw channel of the abutment if the abutment is affixed onto the implant in the residual tooth area.

30. Method according to claim 23, wherein an outer shape of the abutment is determined by using the second data set, wherein the outer shape of the abutment is restricted by at least one of an arrangement of adjacent teeth, a direction by which the abutment is to be affixed onto the implant, and attachment of the abutment in the implant.

31. Method according to claim 23, wherein the affixability of the abutment onto the implant in the residual tooth area is checked.

32. Method according to claim 23, wherein an inner shape of the dental prosthesis part is determined by the outer shape of the abutment.

33. System including a processor and a non-transitory computer-readable medium with instructions that when loaded into the processor execute a method according to claim 23.

34. System for modelling an individual dental prosthesis that comprises an abutment, the system comprising a detection device that ascertains a first data set and a second data set and a processor that determines a direction of insertion by which a dental prosthesis part is to be pushed onto the abutment, wherein:
the first data set describes a first three-dimensional geometry, wherein this first geometry comprises a residual tooth area that is to be provided with a dental prosthesis, as well as at least one implant onto which an auxiliary element is affixed, and
the second data set describes a second three-dimensional geometry, wherein this second geometry comprises the residual tooth area that is to be provided with a dental prosthesis, as well as at least one implant onto which no auxiliary element is affixed,
and further comprising
non-transitory computer readable medium with instructions that when loaded into the processor execute a method wherein,
by using the second data set or by using the first data set and the second data set, the direction of insertion can be determined by which a dental prosthesis part is to be pushed onto the abutment, including determining with the first data set the position of the manipulation implant in the model of the residual tooth area, wherein consequently the position of the implant in the residual tooth area can be determined precisely by the affixed auxiliary element, and determining with the second data set that all areas of the model of the residual tooth area are described.

35. System comprising a processor and a non-transitory computer-readable data medium with instructions that, when loaded in the processor, execute a method comprising automatically determining a direction of insertion for a dental prosthesis part, the method comprising steps of:
wherein three or more tangents are laid on the edges of a ground tooth and/or of an abutment that is located in a residual tooth area that is to be provided with a dental prosthesis, a cone envelope is specified around the ground tooth and/or the abutment by the tangents, and wherein the aperture angle of the cone defines an angular range for the direction of insertion,
and the processor executes a method wherein an additional ground tooth and/or an additional abutment is located in the residual tooth area, wherein the additional ground tooth and/or the additional abutment is to be provided with an additional or the same dental prosthesis, wherein three additional or more tangents are laid on the additional ground tooth and/or on the additional abutment, an additional cone envelope is specified around the additional ground tooth and/or the additional abutment, wherein an angular range results for the direction of insertion from an intersection of the two aperture angles of the two cones.

* * * * *